(12) United States Patent
Feng et al.

(10) Patent No.: US 11,407,734 B2
(45) Date of Patent: Aug. 9, 2022

(54) PREPARATION METHOD FOR TYROSINE KINASE INHIBITOR AND INTERMEDIATE THEREOF

(71) Applicant: JIANGSU HENGRUI MEDICINE CO., LTD., Jiangsu (CN)

(72) Inventors: Guobing Feng, Jiangsu (CN); Yongxing Cao, Jiangsu (CN); Peng Zhang, Jiangsu (CN); Zhenjun Qiu, Jiangsu (CN); Long Zhang, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 20 days.

(21) Appl. No.: 16/756,782

(22) PCT Filed: Oct. 17, 2018

(86) PCT No.: PCT/CN2018/110615
§ 371 (c)(1),
(2) Date: Apr. 16, 2020

(87) PCT Pub. No.: WO2019/076316
PCT Pub. Date: Apr. 25, 2019

(65) Prior Publication Data
US 2020/0239443 A1    Jul. 30, 2020

(30) Foreign Application Priority Data

Oct. 18, 2017 (CN) .......................... 201710978352.8

(51) Int. Cl.
*C07D 401/14* (2006.01)
*C07D 401/12* (2006.01)
(52) U.S. Cl.
CPC ......... *C07D 401/14* (2013.01); *C07D 401/12* (2013.01)

(58) Field of Classification Search
None
See application file for complete search history.

(56) References Cited

U.S. PATENT DOCUMENTS

2006/0270669 A1* 11/2006 Chew ................... C07D 215/38
514/232.5

FOREIGN PATENT DOCUMENTS

| CN | 101180269 A | 5/2008 |
|----|-------------|--------|
| CN | 101478964 A | 7/2009 |
| CN | 102020639 A | 4/2011 |
| CN | 105330646 A | 7/2016 |
| EP | 2684877 A2 | 1/2014 |
| WO | 2005019201 A2 | 3/2005 |
| WO | 2006127205 A2 | 11/2006 |

OTHER PUBLICATIONS

Gu, Ning et al. "The Wittig-Horner reaction for the synthesis of neratinib" Research on Chemical Intermediates, vol. 39, No. 7, 2013, pp. 3105-3110, 12 pages.
International Search Report dated Jan. 17, 2019 in corresponding International application No. PCT/CN2018/110615.
Schafer Harry et al., "Zur Synthese Von 4-Aminochinolinen Durch Intramolekularo Friedel-Crafts-Reaktion" Monatshefte fur Chemie, No. 109, Dec. 31, 1978, pp. 527-535.

* cited by examiner

*Primary Examiner* — Heidi Reese
(74) *Attorney, Agent, or Firm* — Ice Miller LLP

(57) ABSTRACT

Provided is a preparation method for a tyrosine kinase inhibitor and an intermediate thereof. Specifically, a preparation method for a cyanoquinoline compound is provided. The method has a high yield, good product purity, and mild reaction conditions.

19 Claims, No Drawings

PREPARATION METHOD FOR TYROSINE KINASE INHIBITOR AND INTERMEDIATE THEREOF

CROSS-REFERENCE TO RELATED APPLICATIONS

This application is a Section 371 of International Patent Application No. PCT/CN2018/110615, filed Oct. 17, 2018, which was published in the Chinese language on Apr. 25, 2019, under International Publication No. WO 2019/076316 A1, which claims priority under 35 U.S.C. § 119(b) to Chinese Patent Application No. 201710978352.8, filed Oct. 18, 2017, the disclosure of all of which are incorporated herein by reference in their entireties.

FIELD OF INVENTION

The present invention belongs to pharmaceutical field, which relates to a preparation method for a tyrosine inhibitor and an intermediate thereof.

PRIOR ARTS

In recent years, the mortality rate of tumors in China has been increasing. The mortality rate of malignant tumors in urban residents is about 100-200/100,000, and cancer threatens people's lives and quality of life seriously. Chemotherapy or radiotherapy using traditional chemotherapy drugs is highly toxic and poorly specific for the proliferation of malignant tumors. Therefore, it is a very challenging and significant topic in life sciences today to find effective and low-toxic antitumor drugs. Receptor tyrosine kinases are a class of transmembrane proteins involved in signal transduction, which are expressed in a variety of cells, and regulate cell growth, differentiation, and neovascularization. Studies have shown that more than 50% of proto-oncogenes and oncogene products have tyrosine kinase activity, and their abnormal expression will cause tumorigenesis. In addition, they are also closely related to tumor invasion and metastasis, tumor neovascularization, and tumor chemotherapy resistance. Tyrosine kinase inhibitors have been on the market since 2001 and have become a new class of anticancer drugs significantly.

Numerous tyrosine kinase inhibitors have been disclosed in the prior art, such as Canertinib (CI-1033), BIBW-2992, Neratinib (HKI-272) and Pelitinib (EKB-569), etc.

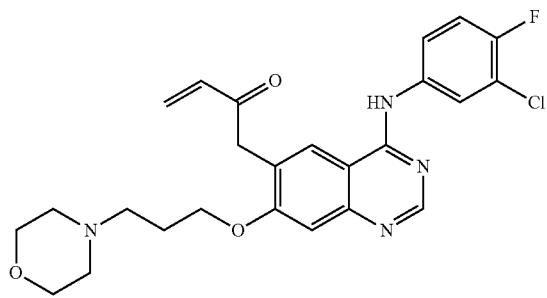

Canertinib

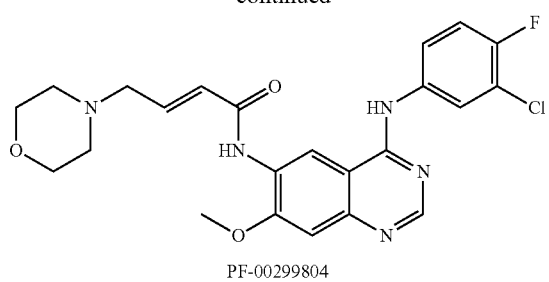

PF-00299804

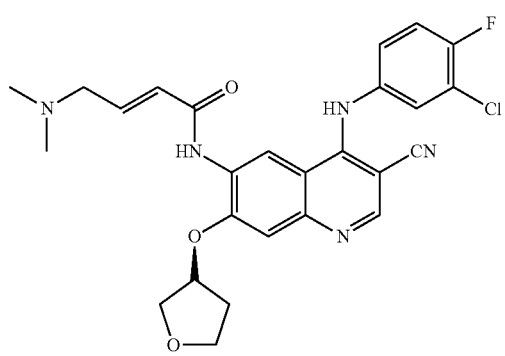

BIBW 2992

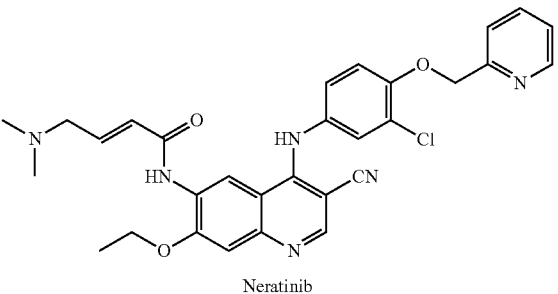

Neratinib

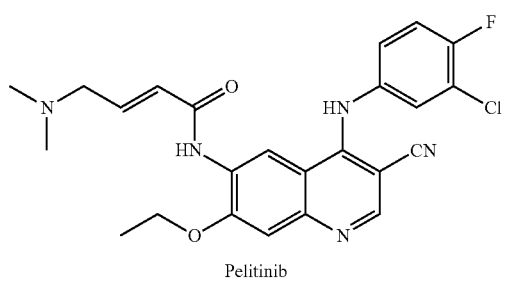

Pelitinib

WO2011029265 discloses an effective tyrosine kinase inhibitor and a preparation method thereof. Its chemical name is (R,E)-N-(4-((3-chloro-4-(pyridin-2-ylmethoxy)phenyl)amino)-3-cyano-7-ethoxyquinolin-6-yl)-3-(1-methylpyrrolidin-2-yl)acrylamide and its structure is represented by formula I. The compound has obvious pharmacodynamic advantages. CN102933574A describes a dimaleate form of the compound, which has improved physical and chemical properties, pharmacokinetic properties and bioavailability.

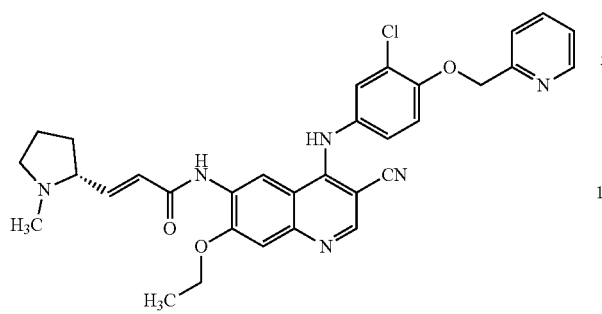

In the preparation process of numerous existing tyrosine kinase inhibitors, the preparation of a cyanoquinoline compound represented by formula II from a compound represented by formula III is a very critical step, which affects the yield and progress of the entire production process.

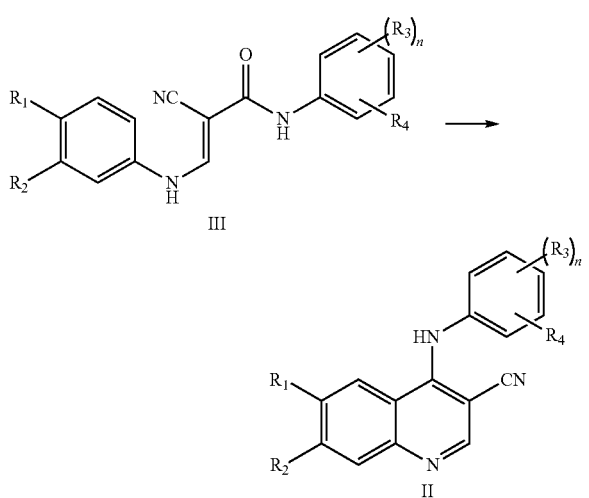

CN101180269A reports a method for preparing the compound represented by formula II by using 10 equivalents of phosphorus oxychloride as a raw material and methanol to catalyze the reaction. The reaction yield is low, the reaction time is long, the reaction product is viscous, the post-treatment is very complicated, and the purity is not high when the method is used for industrial production. At the same time, due to the strong corrosiveness and strong irritation of phosphorus oxychloride, the physical health of production workers is affected seriously when phosphorus oxychloride is used in large quantities; the reaction between methanol and phosphorus oxychloride is violent, and the system temperature is difficult to control, which is easy to cause safety production accidents during large-scale production. Therefore, there is an urgent need for a method for preparing the compound represented by formula II with high yield, good product purity, small amount of phosphorus oxychloride, and mild reaction conditions.

SUMMARY OF THE PRESENT INVENTION

In order to overcome the shortcomings of the prior art, the purpose of the present invention is aimed to provide a new method for preparing a tyrosine inhibitor and an intermediate thereof.

One aspect of the present invention is to provide a method for preparing a compound represented by formula II,

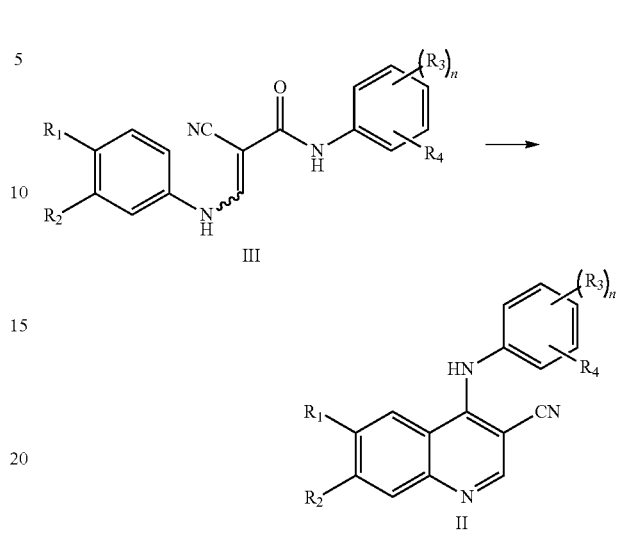

wherein, $R_1$ is selected from the group consisting of hydrogen, alkyl, halogen, hydroxyl, nitro, cyano, alkoxy, phthalimido,

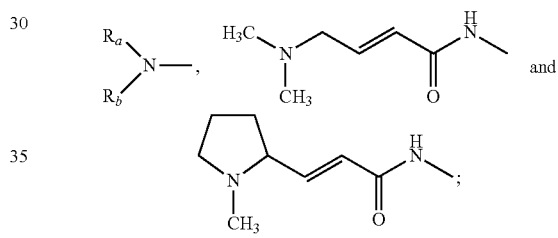

wherein, each of the alkyl, alkoxy is optionally substituted by one or more substituent(s) selected from the group consisting of halogen, hydroxyl, amino, nitro and cyano;

each of $R_a$ and $R_b$ is independently selected from the group consisting of hydrogen, amino protecting group, alkyl, cycloalkyl, alkanoyl, alkenyl, alkynyl, aryl and heteroaryl; wherein, each of the alkyl, cycloalkyl, alkanoyl, alkenyl, alkynyl, aryl and heteroaryl is optionally substituted by one or more substituent(s) selected from the group consisting of halogen, hydroxyl, amino, nitro and cyano;

$R_2$ is selected from the group consisting of hydrogen atom, halogen, hydroxyl and alkoxy;

each of $R_3$ is independently selected from the group consisting of alkyl, halogen, hydroxyl, nitro, cyano and alkoxy;

$R_4$ has the following structure:

T is selected from the group consisting of —(CH$_2$)r-, —O(CH$_2$)r-, —NH(CH$_2$)r- and —S(CH$_2$)r;

L is selected from the group consisting of aryl and heteroaryl, preferably, phenyl, furyl, thienyl, pyridyl, pyrrolyl, N-alkylpyrrolyl, pyrimidinyl, pyrazinyl, imidazolyl and tetrazolyl, each of the aryl and heteroaryl is optionally further substituted by one or more substituent(s) selected from the group consisting of halogen and alkyl;

n is 0, 1, 2, 3 or 4; r is 0, 1 or 2;

the method comprises a step of reacting a compound represented by formula III with phosphorus oxychloride in the presence of a catalyst, wherein, the catalyst includes a catalyst A, and the catalyst A can be one or more selected from the group consisting of water, phosphoric acid and phosphate.

The phosphate can be a metal ion salt or an ammonium salt, and can be, for example, sodium phosphate, disodium hydrogen phosphate, potassium phosphate, ferrous phosphate, sodium dihydrogen phosphate, potassium dihydrogen phosphate, zinc phosphate, ferric phosphate, ammonium phosphate, and the like.

In certain embodiments, the catalyst A is preferably one or more selected from the group consisting of water, phosphoric acid, sodium phosphate, disodium hydrogen phosphate, potassium phosphate, ferrous phosphate, sodium dihydrogen phosphate and potassium dihydrogen phosphate.

The solvent used in the reaction can be a conventional solvent, such as one or more selected from the group consisting of dimethylformamide, 1-methyl-2-pyrrolidone, tetrahydrofuran, methyltetrahydrofuran, dioxane, toluene, xylene, dimethylsulfoxide, ether, isopropyl ether, methyl tert-butyl ether, acetonitrile and propionitrile, and preferably acetonitrile.

The reaction temperature of the reaction can be 0° C. to 200° C., preferably 20° C. to 100° C., and more preferably 40° C. to 80° C.

In certain embodiments, the molar ratio of the compound represented by formula III to phosphorus oxychloride can be 1:1 to 1:20, preferably 1:1 to 1:8.

In certain embodiments, the molar ratio of the compound represented by formula III to the catalyst A can be 1:0.01 to 1:1, preferably 1:0.1 to 1:0.7.

In certain embodiments, the catalyst further comprises a catalyst B, and the catalyst B can be one or more selected from the group consisting of a metal catalyst and a Lewis acid.

The metal catalyst can be a transition metal and the like, such as iron, cobalt, nickel, copper, silver, platinum, gold, palladium, rhodium, zinc, and the like.

The Lewis acid can be aluminum chloride, ferric chloride, boron trifluoride, antimony pentafluoride, niobium pentachloride, zinc chloride, copper chloride, and the like.

Preferred catalyst B can be one or more selected from the group consisting of iron, cobalt, nickel, copper, silver, platinum, gold, palladium, rhodium, zinc, aluminum chloride, ferric chloride, boron trifluoride, antimony pentafluoride, niobium pentachloride, zinc chloride and copper chloride, more preferably aluminum chloride, ferric chloride or zinc chloride.

In certain embodiments, the catalyst used in the reaction can include water and iron, water and copper, water and silver, water and platinum, water and gold, water and aluminum chloride, water and ferric chloride, water and boron trifluoride, water and zinc chloride, water and copper chloride, phosphoric acid and iron, phosphoric acid and copper, phosphoric acid and silver, phosphoric acid and platinum, phosphoric acid and gold, phosphoric acid and aluminum chloride, phosphoric acid and ferric chloride, phosphoric acid and boron trifluoride, phosphoric acid and zinc chloride, phosphoric acid and copper chloride, disodium hydrogen phosphate and iron, disodium hydrogen phosphate and copper, disodium hydrogen phosphate and silver, disodium hydrogen phosphate and platinum, disodium hydrogen phosphate and gold, disodium hydrogen phosphate and aluminum chloride, disodium hydrogen phosphate and ferric chloride, disodium hydrogen phosphate and boron trifluoride, disodium hydrogen phosphate and zinc chloride, disodium hydrogen phosphate and copper chloride, sodium phosphate and iron, sodium phosphate and copper, sodium phosphate and silver, sodium phosphate and platinum, sodium phosphate and gold, sodium phosphate and aluminum chloride, sodium phosphate and ferric chloride, sodium phosphate and boron trifluoride, sodium phosphate and zinc chloride, sodium phosphate and copper chloride, potassium dihydrogen phosphate and iron, potassium dihydrogen phosphate and copper, potassium dihydrogen phosphate and silver, potassium dihydrogen phosphate and platinum, potassium dihydrogen phosphate and gold, potassium dihydrogen phosphate and chloride aluminum, potassium dihydrogen phosphate and ferric chloride, potassium dihydrogen phosphate and boron trifluoride, potassium dihydrogen phosphate and zinc chloride, and potassium dihydrogen phosphate and copper chloride, preferably phosphoric acid and iron, phosphoric acid and ferric chloride, phosphoric acid and zinc chloride, phosphoric acid and aluminum chloride, disodium hydrogen phosphate and aluminum chloride, disodium hydrogen phosphate and ferric chloride, disodium hydrogen phosphate and zinc chloride, or potassium dihydrogen phosphate and zinc chloride.

In certain preferred embodiments, the catalyst used in the reaction can include phosphoric acid and iron, phosphoric acid and ferric chloride, phosphoric acid and aluminum chloride, phosphoric acid and zinc chloride, disodium hydrogen phosphate and zinc chloride, sodium dihydrogen phosphate and aluminum chloride, potassium dihydrogen phosphate and aluminum chloride, potassium dihydrogen phosphate and ferric chloride, or potassium dihydrogen phosphate and zinc chloride.

In certain embodiments, the molar ratio of the compound represented by formula III to the catalyst B can be 1:0.01 to 1:1, preferably 1:0.1 to 1:0.7.

In certain embodiments, the compound represented by formula III is

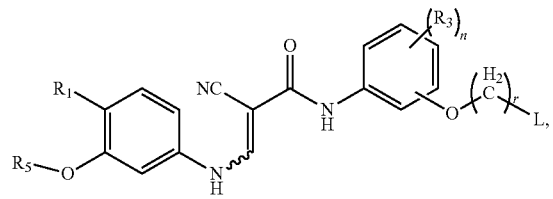

the compound represented by formula II is

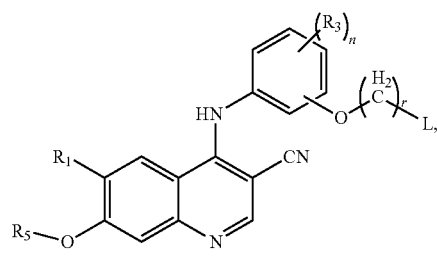

wherein, $R_1$ is selected from the group consisting of phthalimido,

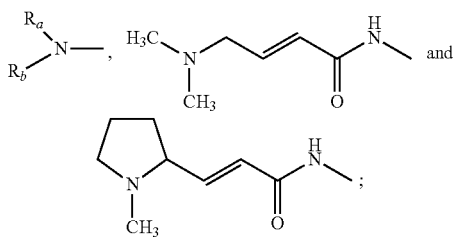

each of $R_a$ and $R_b$ is independently selected from the group consisting of hydrogen, amino protecting group, alkyl, cycloalkyl, alkanoyl, alkenyl, alkynyl, aryl and heteroaryl; wherein, each of the alkyl, cycloalkyl, alkanoyl, alkenyl, alkynyl, aryl and heteroaryl is optionally substituted by one or more substituent(s) selected from the group consisting of halogen, hydroxyl, amino, nitro and cyano;

each of $R_3$ is independently selected from the group consisting of alkyl, halogen, hydroxyl, nitro, cyano and alkoxy;

$R_5$ is $C_1$-$C_6$ alkyl;

L is selected from the group consisting of phenyl, furyl, thienyl, pyridyl, pyrrolyl, N-alkylpyrrolyl, pyrimidinyl, pyrazinyl, imidazolyl and tetrazolyl, and each of the phenyl, furyl, thienyl, pyridyl, pyrrolyl, N-alkylpyrrolyl, pyrimidinyl, pyrazinyl, imidazolyl and tetrazolyl is optionally further substituted by one or more substituent(s) selected from the group consisting of halogen and alkyl;

n is 0, 1, 2, 3 or 4; r is 0, 1 or 2.

In certain embodiments, the compound represented by formula III is

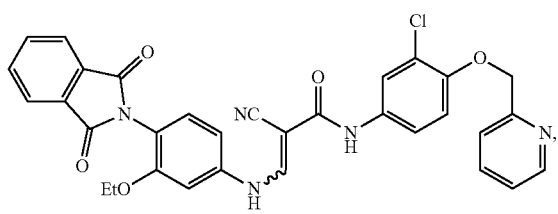 [SMILES: CCOc1cc(NC=C(C#N)C(=O)Nc2ccc(OCc3ccccn3)c(Cl)c2)ccc1N1C(=O)c2ccccc2C1=O]

the compound represented by formula II is

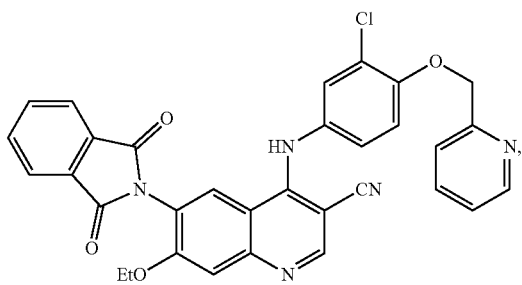 [SMILES: CCOc1cc2ncc(C#N)c(Nc3ccc(OCc4ccccn4)c(Cl)c3)c2cc1N1C(=O)c2ccccc2C1=O]

Another aspect of the present invention is to provide a method for preparing a compound represented by formula II', comprising a step of reacting the compound represented by formula II with a deprotection reagent.

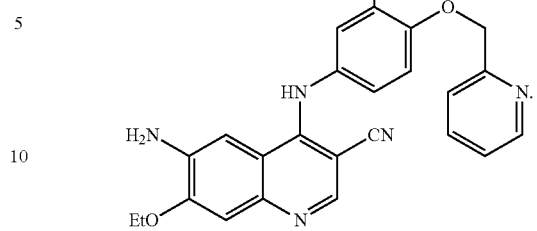

The deprotection reagent can be hydrazine, $NaBH_4$, $KBH_4$, alkylcarboxylic acid (such as formic acid, acetic acid, propionic acid, and the like), inorganic acid (hydrochloric acid, sulfuric acid, and the like), ammonia or amino-substituted $C_1$-$C_6$ alkyl alcohol (aminomethanol, aminoethanol, and the like), preferably amino-substituted $C_1$-$C_6$ alkyl alcohol, and more preferably aminoethanol. The solvent used in the reaction can be a conventional solvent, such as one or more selected from the group consisting of dimethylformamide, 1-methyl-2-pyrrolidone, dimethylsulfoxide, tetrahydrofuran, methyltetrahydrofuran, dioxane, toluene, xylene, dimethylsulfoxide, ether, isopropyl ether, methyl tert-butyl ether, acetonitrile, propionitrile, methanol, ethanol, isopropyl alcohol, and water.

The reaction temperature of the reaction can be 0° C. to 200° C., preferably 20° C. to 100° C., and more preferably 40° C. to 80° C.

The compound represented by formula II can be prepared by the method according to the present invention. When the deprotection reagent is an amino alcohol, the compound represented by formula II' obtained by the reaction has high purity, the by-products are easily removed, the post-treatment is simple and the method is convenient for industrial production.

In certain embodiments, the molar ratio of the compound represented by formula II to the deprotection reagent can be 1:1 to 1:30, preferably 1:1 to 1:15.

Another aspect of the present invention is to provide a method for preparing neratinib or a pharmaceutically acceptable salt thereof, comprising the step of preparing the compound represented by formula II according to the present invention.

Further, the method can further comprise the step of preparing the compound represented by formula II' according to the present invention.

Further, the method can further comprise a step of reacting the compound represented by formula II' with

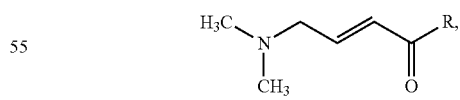

wherein R is selected from the group consisting of hydroxyl, alkoxy and halogen. This reaction can be carried out by the methods disclosed in the prior art (for example, CN100537518C).

Another aspect of the present invention is to provide a method for preparing a compound represented by formula I or a pharmaceutically acceptable salt thereof, comprising the step of preparing the compound represented by formula II according to the present invention.

Further, the method can further comprise the step of preparing the compound represented by formula II' according to the present invention.

Further, the method can further comprise a step of reacting the compound represented by formula II' with

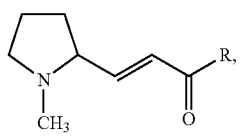

wherein R is selected from the group consisting of hydroxyl, alkoxy and halogen. This reaction can be carried out by the methods disclosed in the prior art.

In certain embodiments, the pharmaceutically acceptable salt of the compound represented by formula I can be p-toluenesulfonate, mesylate, maleate, succinate or malate, preferably maleate, more preferably dimaleate. The salt of the compound represented by formula I can be prepared by the methods disclosed in the prior art (for example, CN102933574A).

Another aspect of the present invention is to provide a method for preparing a compound represented by formula I, comprising, 1) reacting a compound represented by formula IV with phosphorus oxychloride in the presence of a catalyst to prepare a compound represented by formula IV',

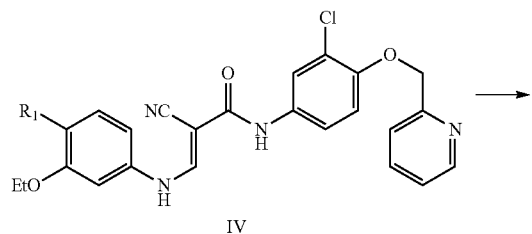

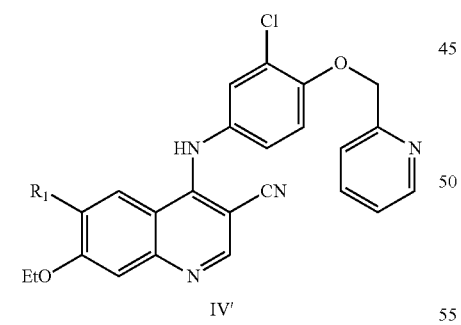

wherein, $R_1$ is selected from the group consisting of phthalimido and

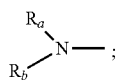

each of $R_a$ and $R_b$ is independently selected from the group consisting of hydrogen and amino protecting group, and $R_a$ and $R_b$ are not hydrogen at the same time;

the catalyst is selected from the group consisting of water, phosphoric acid, sodium phosphate, disodium hydrogen phosphate, potassium phosphate, ferrous phosphate, sodium dihydrogen phosphate, potassium dihydrogen phosphate, phosphoric acid and iron, phosphoric acid and ferric chloride, phosphoric acid and aluminum chloride, phosphoric acid and zinc chloride, disodium hydrogen phosphate and zinc chloride, sodium dihydrogen phosphate and aluminum chloride, potassium dihydrogen phosphate and aluminum chloride, potassium dihydrogen phosphate and ferric chloride, and, potassium dihydrogen phosphate and zinc chloride;

reacting the compound represented by formula IV' with a deprotection reagent to prepare a compound represented by formula II',

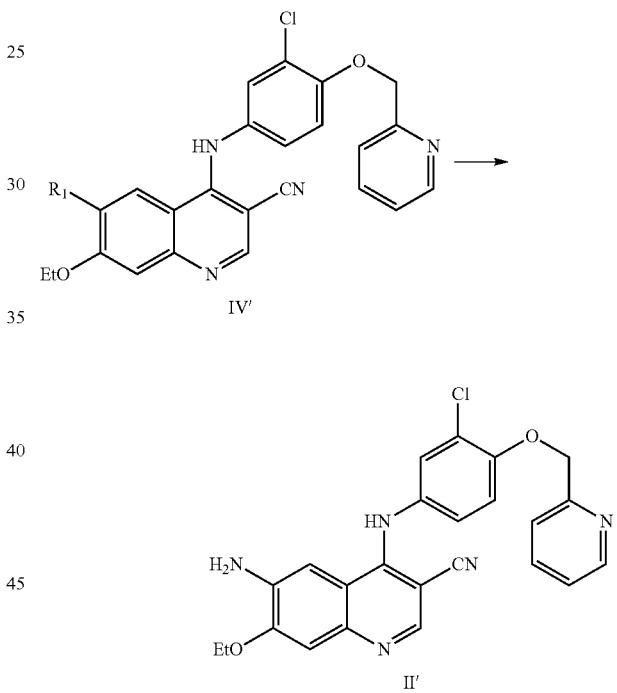

the deprotection agent is selected from the group consisting of hydrazine, $NaBH_4$, $KBH_4$, alkylcarboxylic acid, inorganic acid, ammonia and amino-substituted $C_1$-$C_6$ alkyl alcohol, preferably amino-substituted $C_1$-$C_6$ alkyl alcohol, more preferably aminoethanol;

reacting the compound represented by formula II' with

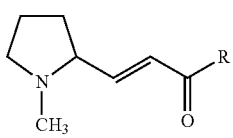

to prepare a compound represented by formula I,

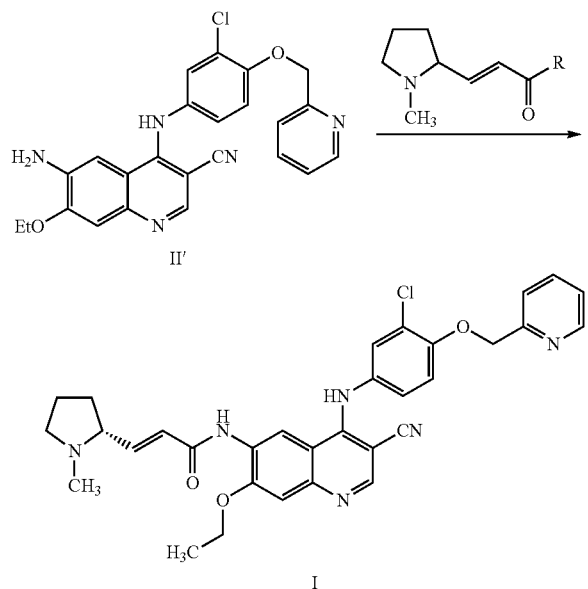

wherein, R is selected from the group consisting of hydroxyl, alkoxy and halogen.

The pharmaceutically acceptable salt of the compound represented by formula I is selected from the group consisting of p-toluenesulfonate, mesylate, maleate, succinate and malate, preferably maleate, more preferably dimaleate.

In certain embodiments, R is hydroxyl, the reaction of the method is carried out in the presence of a condensation agent, and the condensation agent is selected from the group consisting of DCC, EDC, BOP, HBTU and EEDQ, preferably EEDQ.

In the method for preparing the tyrosine kinase inhibitor intermediate of the present invention, the reaction yield and purity is unexpectedly improved greatly, while the amount of phosphorus oxychloride is reduced by selecting different catalysts or combinations of catalysts. Due to the improvement of the reaction yield and purity, the reaction solution can be directly put into the next step of reaction after simple post-treatment, which shortens the product processing time in the production process and greatly improves the production efficiency. In addition, the preparation method of the present invention has mild and controllable reaction conditions, which greatly reduces the safety risk of industrial production.

Unless stated to the contrary, the terms used in the specification and claims have the meanings described below.

The term "alkyl" refers to a saturated aliphatic hydrocarbon group, which is a straight or branched chain group comprising 1 to 20 carbon atoms, preferably an alkyl comprising 1 to 12 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably a lower alkyl comprising 1 to 6 carbon atoms, non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl can be substituted or unsubstituted, and when the alkyl is substituted, the substituent(s) can be substituted at any available connection site. The substituent is preferably one or more group(s) independently selected from the group consisting of alkyl, alkenyl, alkynyl, alkoxy, alkylthio, alkylamino, halogen, mercapto, hydroxyl, nitro, cyano, cycloalkyl, heterocyclyl, aryl, heteroaryl, cycloalkoxy, heterocycyloxy, cycloalkylthio, heterocycloalkylthio, oxo, carboxyl and carboxylate group.

The term "cycloalkyl" refers to a saturated or partially unsaturated monocyclic or polycyclic hydrocarbon substituent group comprising 3 to 20 carbon atoms, preferably 3 to 12 carbon atoms, more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl comprising a spiro ring, a fused ring or a bridged ring.

The term "heterocyclyl" refers to a saturated or partially unsaturated monocyclic or polycyclic hydrocarbon substituent group containing 3 to 20 ring atoms, one or more of which are heteroatoms selected from the group consisting of N, O and $S(O)_m$ (wherein m is an integer of 0 to 2), but excluding —O—O—, —O—S— or —S—S— in the ring, and the remaining ring atoms are carbon atoms. Preferably, the heterocyclyl contains 3 to 12 ring atoms wherein 1 to 4 atoms are heteroatoms; more preferably, the heterocyclyl contains 3 to 6 ring atoms. Non-limiting examples of monocyclic heterocyclyl include pyrrolidnyl, imidazolyl, tetrahydrofuranyl, tetrahydrothienyl, dihydroimidazolyl, dihydrofuryl, dihydropyrazolyl, dihydropyrrolyl, piperidinyl, piperazinyl, morpholinyl, thiomorpholinyl, homopiperazinyl and the like, and preferably piperidinyl or pyrrolidnyl. Polycyclic heterocyclyl includes heterocyclyl comprising a spiro ring, a fused ring or a bridged ring.

The term "aryl" refers to a 6 to 14 membered all-carbon monocyclic ring or fused polycyclic ring (that is, ring shares an adjacent pair of carbon atoms) having a conjugated π-electron system, preferably 6 to 10 membered aryl, for example, phenyl and naphthyl. The aryl ring can be fused to a heteroaryl ring, a heterocyclyl ring or a cycloalkyl ring, wherein the ring connected to the parent structure is an aryl ring, and non-limiting examples include:

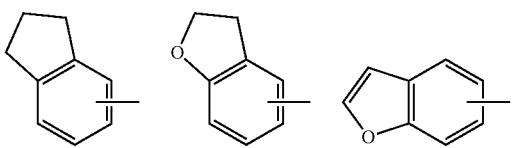

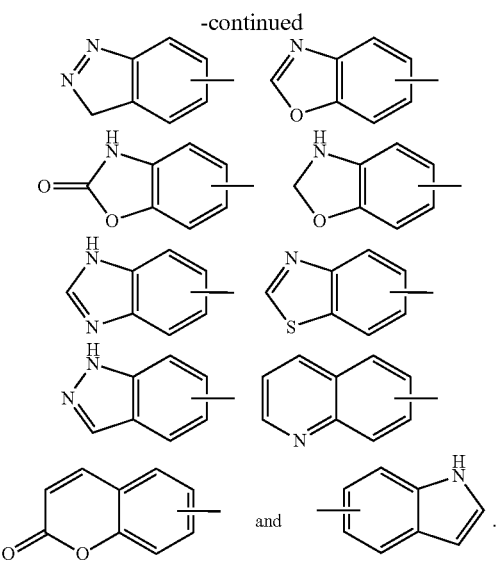

The aryl can be substituted or unsubstituted, and when substituted, the substituent(s) is preferably one or more group(s) independently selected from the following group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl and carboxylate group, preferably phenyl.

The term "heteroaryl" refers to a 5 to 14 membered heteroaromatic system comprising 1 to 4 heteroatoms selected from the group consisting of O, S and N. The heteroaryl is preferably 5 to 12 membered heteroaryl, for example, imidazolyl, furyl, thienyl, thiazolyl, pyrazolyl, oxazolyl, pyrrolyl, tetrazolyl, pyridyl, pyrimidinyl, thiadiazole, pyrazinyl and the like, preferably imidazolyl, pyrazolyl, pyrimidinyl or thiazolyl; more preferably pyrazolyl or thiazolyl. The heteroaryl ring can be fused to an aryl ring, a heterocyclyl ring or a cycloalkyl ring, wherein the ring connected to the parent structure is a heteroaryl ring and non-limiting examples include:

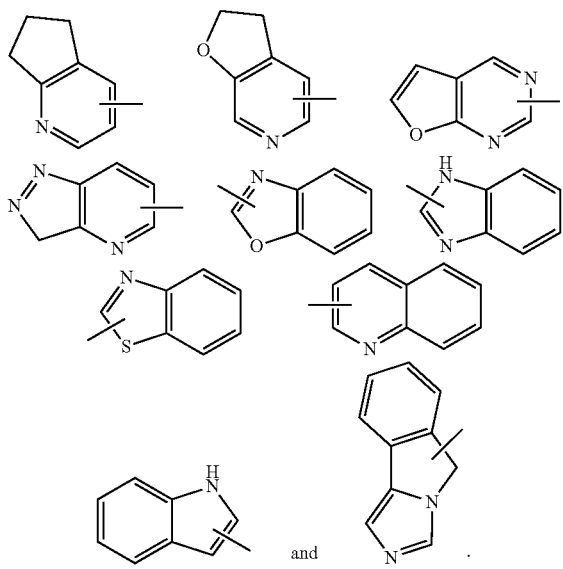

The heteroaryl can be optionally substituted or unsubstituted, and when substituted, the substituent(s) is preferably one or more group(s) independently selected from the following group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl and carboxylate group.

The term "alkoxy" refers to an —O-(alkyl) or an —O-(unsubstituted cycloalkyl), wherein the definition of alkyl is as defined above. Non-limiting examples of alkoxy include: methoxy, ethoxy, propoxy, butoxy, cyclopropyloxy, cyclobutyloxy, cyclopentyloxy, cyclohexyloxy. The alkoxy can be optionally substituted or unsubstituted, and when substituted, the substituent(s) is preferably one or more group(s) independently selected from the following group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio, carboxyl and carboxylate group.

The term "halogen" refers to fluorine, chlorine, bromine or iodine.

"Amino protecting group" is an appropriate amino protecting group known in the art, see amino protecting group in the literature ("Protective Groups in Organic Synthesis", $5^{Th}$. Ed. T. W Greene & P. G. M Wuts), preferably, the amino protecting group can be a $C_{1-10}$ alkylacyl or an arylacyl, for example: formyl, acetyl, benzoyl, phthaloyl, and the like; it can be a $C_{1-6}$ alkylsulfonyl or a $C_{6-10}$ arylsulfonyl; it can also be a $C_{1-6}$ alkoxycarbonyl or a $C_{6-10}$ aryloxycarbonyl, Boc or Cbz; it can also be an alkyl, for example trityl (Tr), 2,4-dimethoxybenzyl (DMB), p-methoxybenzyl (PMB) or benzyl (Bn).

"Optional" or "optionally" means that the event or circumstance described subsequently can, but does not have to occur, and such a description includes the situation in which the event or circumstance occurs or does not occur. For example, "the heterocyclyl optionally substituted by alkyl" means that alkyl can, but need not exist, and such a description includes the situation of the heterocyclyl being substituted by alkyl and the heterocyclyl being not substituted by alkyl.

In the chemical structure of the compound of the present invention, the bond "/" does not specify a configuration, that is, if there is configurational isomerism in the chemical structure, the bond "/" can be " ⋯ " or " ╱ ", or it can contain both " ⋯ " and " ╱ " configuration.

Unless stated to the contrary, the abbreviations used in the specification and claims have the meanings described below.

| Abbreviation | Full name |
|---|---|
| $Et_3N$ | Triethylamine |
| DBU | 1,8-Diazabicyclo[5.4.0]undec-7-ene |
| TMG | N,N,N',N'-tetramethylguanidine |
| Py | Pyridine |
| DIPEA | Ethyldiisopropylamine |
| NaOMe | Sodium methoxide |
| NaOEt | Sodium ethoxide |
| $NaO^tBu$ | Sodium tert-butoxide |
| PCC | Pyridinium chlorochromate |
| EEDQ | 2-Ethoxy-1-ethoxycarbonyl-1,2-dihydroquinoline |
| DMAC | N,N-dimethylacetamide |

DETAILED DESCRIPTION OF THE PREFERRED EMBODIMENT

The following will explain the present invention in detail in conjunction with specific examples, so that those skilled in the art can more fully understand the present invention. The following examples further illustrate the present invention, but the present invention is not limited thereto.

Test conditions of the instrument used in the embodiments:

1. Nuclear Magnetic Resonance Spectrometer (NMR)

Instrument model: Bruker Avance III 400NMR, internal standard: maleic acid; reagent: $d_6$-DMSO;

NMR quantitative test conditions: a certain amount of maleic acid and a sample were accurately weighed and added to the same NMR tube, and $d_6$-DMSO was added by shaking until they were completely dissolved, and then quantitative hydrogen spectrum detection was carried out.

Embodiment 1

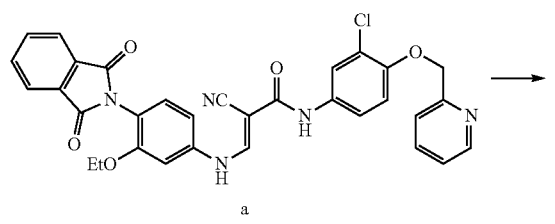

a

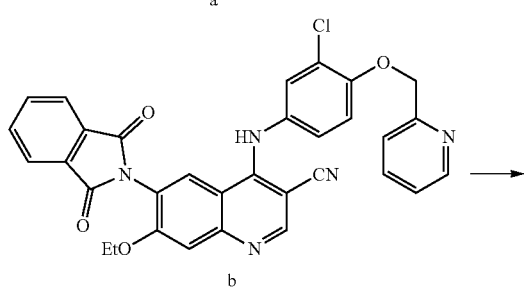

b

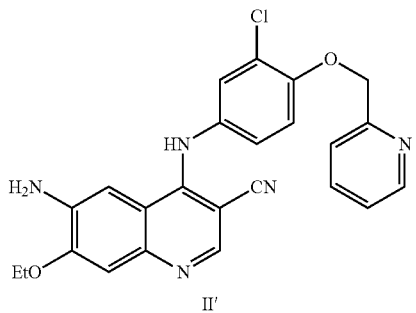

II'

Step 1

Compound a (1.0 eq, 40.0 g, prepared according to the method disclosed in CN101180269A), 390 mL of acetonitrile and 85% phosphoric acid (0.6 eq, 3.96 g) were sequentially added into a 1 L reaction flask, stirred and heated to 60° C.; phosphorus oxychloride (5.0 eq, 51.62 g) was added into the reaction solution dropwise, and the resulting mixture was heated to reflux for 4 h after the dropwise addition. The reaction was cooled to 10° C., and 200 mL of water and 160 mL of ammonia water were sequentially added dropwise to adjust the pH to 8. The reaction solution was directly used in the next step without further purification.

Step 2

Aminoethanol (10.0 eq, 41.13 g) was added to the reaction solution, and the mixture was heated to 50° C. for 3h, and then was cooled to room temperature. The filter cake was filtered by suction filtration and washed with acetonitrile aqueous solution, and the filter cake was slurried with ethanol aqueous solution and 14.05 g of the compound represented by formula II' was obtained by suction filtration with a HPLC purity of 94% and a yield of 46.6% in two steps.

Embodiment 2

Step 1

520 kg of acetonitrile, zinc chloride (0.3 eq, 4522.5 g) and 85% phosphoric acid (0.6 eq, 6.5 kg) were added into a 3000 L reactor, and 65.70 kg of compound a was added under stirring, and the reaction solution was heated to 60° C. and phosphorus oxychloride (5.0 eq, 84.8 kg) was added dropwise, and the mixture was heated to reflux for 35 h after the dropwise addition. The reaction solution was cooled down to below 20° C., and 320 kg of water was added dropwise to quench the reaction. Ammonia was added dropwise after the completion of the dropwise addition to adjust the pH to 8. The reaction solution was directly used in the next step without further purification.

Step 2

Aminoethanol (10.0 eq, 70. 0 kg) was added to the reaction solution, and the mixture was heated to 60° C. to react for 4 h. The reaction solution was cooled to below 20° C., and centrifugally filtered, and the filter cake was washed with 200 kg of purified water, and after washing, the filter cake was slurried with a mixed solvent of 130 kg of 95% ethanol and 250 kg of water at room temperature for 2 h, and then filtered to dryness to obtain 23.08 kg of the compound represented by formula II'. (HPLC purity 93%, total yield 46.8% in two steps)

Embodiment 3

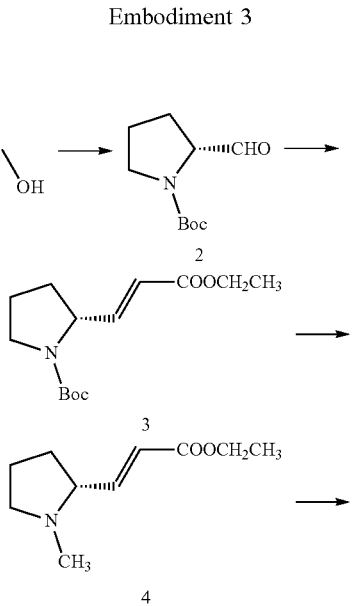

17

-continued

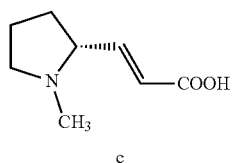

c

Step 1

8.0 kg of compound 1, 264 kg of dichloromethane, 13.0 kg of anhydrous sodium acetate were added into a 300 L reactor and stirred, and the reaction system was cooled to 0° C. by frozen brine, and 17.14 kg of PCC was added in batches under nitrogen protection. The frozen brine was removed after the addition, and the reaction was allowed to naturally warm up to react for 5 h. After TLC test (ethyl acetate: petroleum ether=1:3) showed that the reaction was completed, the reaction solution was filtrated, and the filtrate was concentrated under reduced pressure to obtain a black oil. The product was eluted by column chromatography (eluent: ethyl acetate: petroleum ether=1:3), and the desired component was collected and concentrated under reduced pressure, and 64 kg of ethyl acetate was added to dissolve, the mixture was washed with 0.5 N dilute hydrochloric acid solution, and then washed with water, saturated brine in turn, dried over anhydrous sodium sulfate, and concentrated to obtain 6.42 kg of pale yellow oil.

114 kg of dichloromethane and 3.05 kg of 60% sodium hydride were added into a 300 L reactor and stirred evenly, and the reaction system were cooled by frozen brine, and 7.66 kg of triethylphosphorylacetate was added dropwise and the addition was completed in about 30 minutes, and the reaction solution was stirred at room temperature until no bubbles were generated. A solution of 6.4 kg of the compound 2 obtained in the previous step in dichloromethane (85 kg) was added slowly, and the addition was completed in about 1 h, and the mixture reacted at room temperature for 1.5 to 2 h. After TLC test shown that the reaction was completed, the reaction solution was cooled by frozen brine and ammonium chloride aqueous solution (1.26 kg of ammonium chloride was dissolved in 4.0 kg of water) was slowly added until no bubbles were generated, and the mixture was stirred for about 0.5 h, and then purified water was slowly added dropwise until the reaction mixture became clear, the layers were separated, and the aqueous phase was extracted once with dichloromethane, and the organic phases were combined and washed with saturated sodium hydrogen carbonate aqueous solution and saturated brine, and the organic phase was dried over anhydrous sodium sulfate and concentrated to obtain the crude product ester, which was eluted through column chromatography (eluent: ethyl acetate: petroleum ether=1:8), and the desired component was collected and concentrated under reduced pressure to obtain 4.82 kg of compound 3 with a yield of 45.0%.

Step 2

4.8 kg of the compound 3 and 58.6 kg of formic acid were added into a 100 L reactor, and stirred at room temperature for 15 min, and then 2.63 kg of paraformaldehyde was added. The reaction was refluxed mildly at 90° C. for 3 to 4 hours. TLC test showed that the raw material point disappeared, and then most of the formic acid in the reaction solution was concentrated (remaining about ⅕), and 1M hydrochloric acid was added to adjust the pH to 1.0, the reaction solution was washed with ethyl acetate, and then saturated potassium carbonate aqueous solution was added to adjust the pH to 8.0, extracted with ethyl acetate, the organic phases were combined and washed with saturate sodium chloride aqueous solution, dried over anhydrous sodium sulfate, filtered, and the filtrate was concentrated to obtain a total of 2.42 kg of compound 4 with a yield of 73.5%.

Step 3

2.4 kg of the compound 4 was added into a 20 L reaction flask, and then was added 5.9 kg of methanol, and the reaction temperature was controlled to be no more than 30° C., and 1.49 kg of potassium hydroxide was added in batches, and the addition was completed in about 1.5 h, and the mixture reacted at 30° C. for 2 h. After TLC test showed that the reaction was completed, the reaction was adjusted to the pH to 4 to 5 with 4 N hydrochloric acid in methanol in an ice bath, the mixture was filtered, and the filtrate was concentrated to dryness. 2.7 kg of acetonitrile was added to stir and crystallize, and the resulting mixture was filtered to obtain 1.06 kg of compound c with a yield of 52.1%.

Embodiment 4

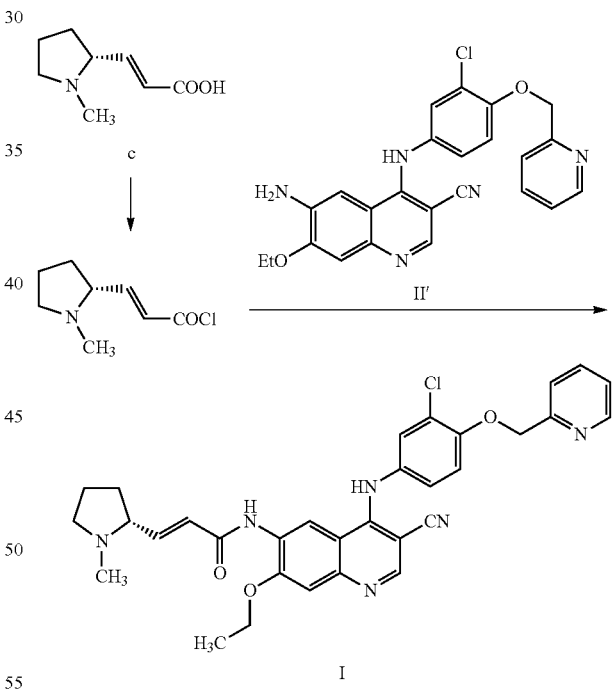

1.0 kg of compound c and 9.4 kg of acetonitrile were added into a 20 L reaction flask, and 30 g of N,N-dimethylformamide was added dropwise. 630 g of oxalyl chloride was then slowly added dropwise in an ice water bath. After the dropwise addition, the reaction solution was stirred at 20° C. for 5 h. A small amount of solids remained at the bottom of the reaction solution, and the reaction solution was directly subjected to a condensation reaction in the next step without treatment.

1.15 kg of compound II' was dissolved in 7.2 kg of N-methylpyrrolidone, and the mixture was stirred for 10 min. The reaction solution from the previous step was added dropwise in an ice water bath, and was stirred at room temperature overnight. TLC test showed that the reaction was completed. The reaction solution was poured into warm water (45.0 kg) at about 40° C., and stirred and 10% sodium hydroxide solution was slowly added to adjust the pH to 10. The precipitated yellow solid was filtered, and the obtained filter cake was slurried with warm water (about 5.0 kg) at 40° C., and then filtered, the filter cake was dissolved in dichloromethane and the water was separated, then the organic phase was dried and concentrated, and purified by column chromatography. Gradient elution, the initial eluent was dichloromethane: methanol=25:1, and finally was increased to 15:1. The desired component was collected and concentrated to obtain 1.12 kg of Compound I with a yield of 74.5%.

Comparative Embodiment 1

Step 1

According to the method of embodiment 5 in CN101180269A, the material mass of compound a was 27 kg, the material mass of phosphorus oxychloride was 69.7 kg (10.0 eq), and the amount of methanol was 13.5 L to obtain 20 kg of compound b (the purity was 35% detected by quantitative hydrogen spectrum detection (internal standard method), and the actual yield was 26.7%).

Step 2

According to the method of embodiment 6 in CN101180269A, the compound b obtained in the previous step was put into the reaction to obtain 4.0 kg of compound II' with a HPLC purity of 93%. (Total yield was 19.7% in two steps).

Comparative Embodiment 2

Compound a (1.0 eq, 40.0 g), 390 mL of acetonitrile, and 85% phosphoric acid (0.6 eq, 3.96 g) were sequentially added into a 1 L reaction flask, and stirred and heated to 60° C.; phosphorus oxychloride (5.0 eq, 51.62 g) was added to the reaction solution, warmed to reflux for 4 h after the dropwise addition. The reaction was cooled to 10° C., and 200 mL of water and 160 mL of ammonia water were sequentially added dropwise to adjust the pH to 8.

30 mL of ammonium hydroxide and 50 mL of ethanol were added into the reaction solution above, and the reaction mixture was heated to reflux and reacted for 4 h, and then cooled to room temperature, filtered by suction filtration and the filter cake was washed with acetonitrile aqueous solution, the filter cake was slurried with ethanol aqueous solution for 2 h, and filtered by suction to obtain 12 g product (two-step yield of 43%, HPLC: 93%), and the product contained trace (about 0.3%) by-product phthalimide, which was difficult to remove in subsequent reactions.

Comparative Embodiment 3

Compound a (1.0 eq, 80.0 g), 800 mL of acetonitrile, and 40 mL of methanol were sequentially added to a 3 L reaction flask, and stirred and heated to 60° C.; phosphorus oxychloride (5.0 eq, 103.2 g) was added dropwise to the reaction solution, and after the completion of the dropwise addition, the mixture was heated 65° C. to 70° C. and reacted for 54 hours, TLC test showed that there were still much unreacted compound a, and the post-treatment was difficult, and the reaction yield could not be calculated.

Since the present invention has been described according to its particular embodiments, certain modifications and equivalent variations will be apparent to those skilled in the art and are included within the scope of the invention.

What is claimed is:

1. A method for preparing a compound represented by formula II, comprising reacting a compound represented by formula III with phosphorus oxychloride in the presence of a catalyst,

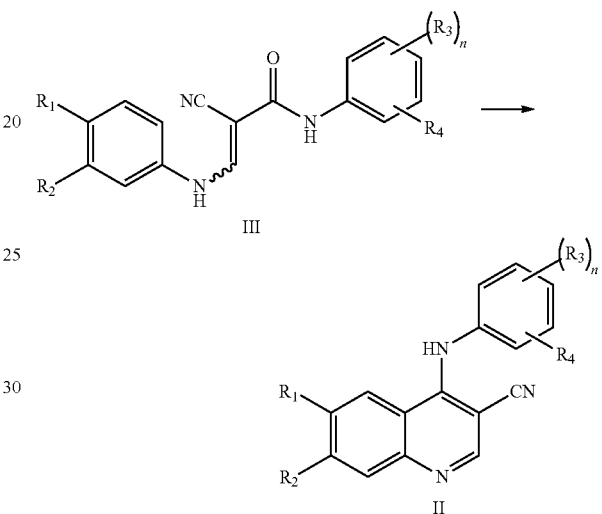

wherein, $R_1$ is phthalimido;

$R_2$ is selected from the group consisting of hydrogen, halogen, hydroxyl and alkoxy;

each of $R_3$ is independently selected from the group consisting of alkyl, halogen, hydroxyl, nitro, cyano and alkoxy;

$R_4$ has the following structure:

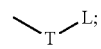

T is selected from the group consisting of -$(CH_2)r$-, -$O(CH_2)r$-, -$NH(CH_2)r$- and -$S(CH_2)r$;

L is selected from the group consisting of aryl and heteroaryl, and each of the aryl and heteroaryl is optionally further substituted by one or more substituent(s) selected from the group consisting of halogen and alkyl;

n is 0, 1, 2, 3 or 4; r is 0, 1 or 2;

the catalyst comprises a catalyst A, and the catalyst A is phosphoric acid.

2. The method of claim 1, wherein the molar ratio of the compound represented by formula III to the catalyst A is 1:0.01 to 1:1.

3. The method of claim 1, wherein the compound represented by formula II is

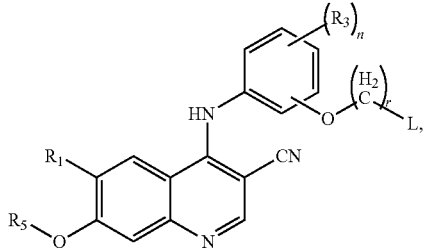

wherein,

R₁ is phthalimido each of R₃ is independently selected from the group consisting of alkyl, halogen, hydroxyl, nitro, cyano and alkoxy;

R₅ is $C_1$-$C_6$ alkyl;

L is selected from the group consisting of phenyl, furyl, thienyl, pyridyl, pyrrolyl, N-alkylpyrrolyl, pyrimidinyl, pyrazinyl, imidazolyl and tetrazolyl, and each of the phenyl, furyl, thienyl, pyridyl, pyrrolyl, N-alkylpyrrolyl, pyrimidinyl, pyrazinyl, imidazolyl and tetrazolyl is optionally further substituted by one or more substituent(s) selected from the group consisting of halogen and alkyl;

n is 0, 1, 2, 3 or 4; and r is 0, 1 or 2.

4. The method of claim 3, wherein the compound represented by formula II is

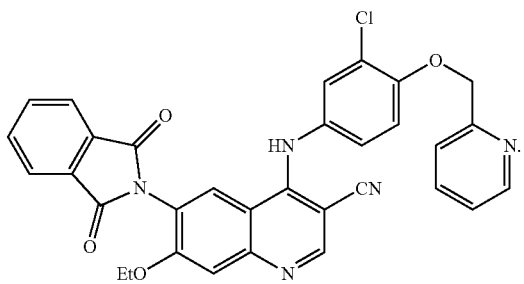 [SMILES: CCOc1cc2ncc(C#N)c(Nc3ccc(OCc4ccccn4)c(Cl)c3)c2cc1N1C(=O)c2ccccc2C1=O]

5. The method of claim 1, wherein the catalyst further comprises a catalyst B, and the catalyst B is one or more selected from the group consisting of a metal catalyst and a Lewis acid.

6. The method of claim 5, wherein the catalyst comprises phosphoric acid and iron, phosphoric acid and ferric chloride, phosphoric acid and aluminum chloride, phosphoric acid and zinc chloride.

7. The method of claim 5, wherein the molar ratio of the compound represented by formula III to the catalyst B is 1:0.01 to 1:1.

8. A method for preparing a compound represented by formula II', comprising preparing a compound represented by formula II according to the method of claim 1, and further comprising reacting the compound represented by formula II with a deprotection reagent,

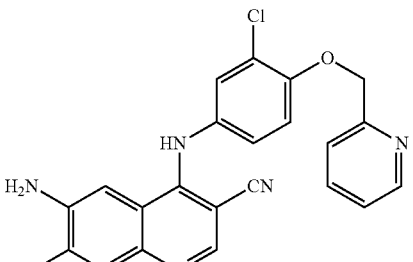

wherein the deprotection reagent is selected from the group consisting of hydrazine, NaBH₄, KBH₄, alkylcarboxylic acid, inorganic acid, ammonia and amino-substituted $C_1$-$C_6$ alkyl alcohol.

9. A method for preparing neratinib or a pharmaceutically acceptable salt thereof, comprising preparing a compound represented by formula II according to the method of claim 1.

10. The method of claim 9, wherein the method further comprises reacting the compound represented by formula II with a deprotection reagent,

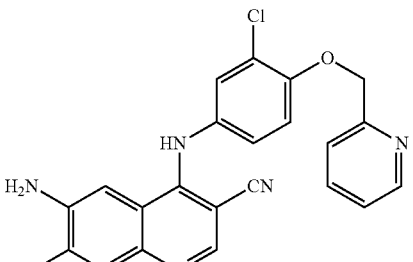

wherein the deprotection reagent is selected from the group consisting of hydrazine, NaBH₄, KBH₄, alkylcarboxylic acid, inorganic acid, ammonia and amino-substituted $C_1$-$C_6$ alkyl alcohol.

11. The method as defined in claim 10, wherein the method further comprises

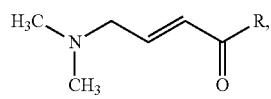

reacting the compound represented by formula II' with wherein R is selected from the group consisting of hydroxyl, alkoxy and halogen.

12. A method for preparing a compound represented by formula I or a pharmaceutically acceptable salt thereof, comprising preparing a compound represented by formula II according to the method of claim 1, 13. The method of claim 12, wherein the method further comprises reacting the compound represented by formula II with a deprotection reagent,

II' wherein the deprotection reagent is selected from the group consisting of hydrazine, NaBH$_4$, KBH$_4$, alkylcarboxylic acid, inorganic acid, ammonia and amino-substituted C$_1$-C$_6$ alkyl alcohol.

14. The method of claim 13, wherein the method further comprises reacting the compound represented by formula II' with wherein R is selected from the group consisting of hydroxyl, alkoxy and halogen.

15. The method of claim 12, wherein the pharmaceutically acceptable salt of the compound represented by formula I is selected from the group consisting of p-toluenesulfonate, mesylate, maleate, succinate and malate.

16. A method for preparing a compound represented by formula I, comprising,
  1) reacting a compound represented by formula IV with phosphorus oxychloride in the presence of a catalyst to prepare a compound represented by formula IV',

IV

IV' wherein,
  R$_1$ is phthalimido;
  the catalyst is selected from the group consisting of, phosphoric acid, phosphoric acid and iron, phosphoric acid and ferric chloride, phosphoric acid and aluminum chloride, phosphoric acid and zinc chloride;
  2) reacting the compound represented by formula IV' with a deprotection reagent to prepare a compound represented by formula II',

IV'

II' wherein the deprotection agent is selected from the group consisting of hydrazine, NaBH$_4$, KBH$_4$, alkylcarboxylic acid, inorganic acid, ammonia and amino-substituted C$_1$-C$_6$ alkyl alcohol;

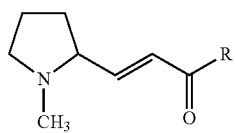

3) reacting the compound represented by formula II' with to prepare a compound represented by formula I,

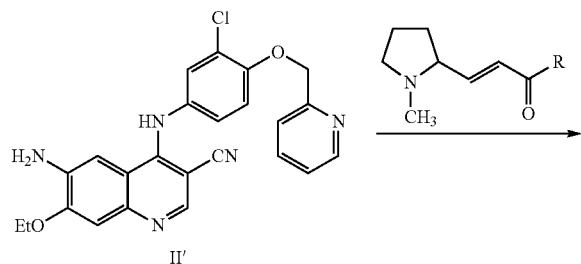

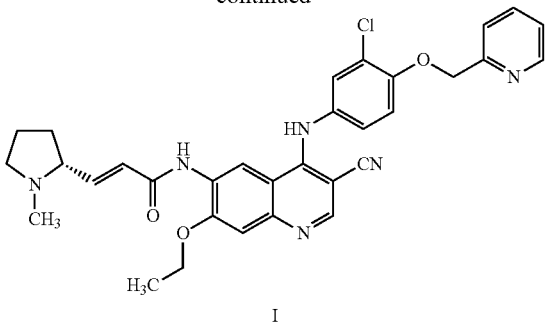

wherein R is selected from the group consisting of hydroxyl, alkoxy and halogen.

17. The method of claim 16, wherein the pharmaceutically acceptable salt of the compound represented by formula I is selected from the group consisting of p-toluenesulfonate, mesylate, maleate, succinate and malate.

18. The method of claim 16, wherein, R is hydroxyl, the method comprises a reaction carried out in the presence of a condensation agent, and the condensation agent is selected from the group consisting of DCC, EDC, BOP, HBTU and EEDQ.

19. The method of claim 5, the catalyst B is one or more selected from the group consisting of iron, cobalt, nickel, copper, silver, platinum, gold, palladium, rhodium, zinc, aluminum chloride, ferric chloride, boron trifluoride, antimony pentafluoride, niobium pentachloride, zinc chloride and copper chloride.

* * * * *